United States Patent [19]

Kaplan

[11] 4,362,820

[45] Dec. 7, 1982

[54] PROCESS FOR PRODUCING ETHYLENE GLYCOL AND METHANOL

[75] Inventor: Leonard Kaplan, Dunbar, W. Va.

[73] Assignee: Union Carbide Corporation, Danbury, Conn.

[21] Appl. No.: 278,900

[22] Filed: Jun. 29, 1981

[51] Int. Cl.³ ............................................. C07C 27/06
[52] U.S. Cl. ................................. 518/700; 252/431 R
[58] Field of Search .............................. 518/700, 715

[56] References Cited

U.S. PATENT DOCUMENTS 2,534,018  12/1950  Gresham et al. .................... 518/700
2,636,046  4/1953   Gresham ............................ 518/715

FOREIGN PATENT DOCUMENTS 655237   12/1947  United Kingdom ................ 518/700
1573422  8/1980   United Kingdom ................ 518/700

*Primary Examiner*—Howard T. Mars
*Attorney, Agent, or Firm*—Gary L. Wamer

[57] ABSTRACT

This invention relates to the manufacture of ethylene glycol, methanol, and derivatives thereof from the reaction of hydrogen and carbon monoxide, by a homogeneous catalytic process using a cobalt-containing compound and an organosilicon compound having least one hydrogen bonded to silicon (—Si—H).

15 Claims, No Drawings

PROCESS FOR PRODUCING ETHYLENE GLYCOL AND METHANOL

BACKGROUND OF THE INVENTION

This invention relates to an improved process, and the catalyst which achieves this process, for making ethylene glycol and methanol directly from synthesis gas, i.e., mixtures of hydrogen and carbon monoxide. More particularly, this invention achieves the production of ethylene glycol and methanol and derivatives thereof directly from synthesis gas in the presence of a cobalt catalyst and an organosilicon compound having a hydrogen bonded to silicon.

The reaction of carbon monoxide and hydrogen in the presence of a cobalt catalyst is disclosed in U.S. Pat. No. 2,636,046, filed Oct. 16, 1948. In this patent, Gresham describes the production of polyfunctional oxygen-containing organic products including such compounds as ethylene glycol, glycerine, and the like.

This is accomplished by the reaction of hydrogen with carbon monoxide in the presence of a solvent to produce glycol. According to this patent, the reaction of carbon monoxide with hydrogen must be at pressures of above 1,000 atmospheres and "particularly above a minimum of about 1,400 atmospheres" in order to obtain the "polyfunctional oxygen-containing organic compounds . . . in excellent yield" (column 2, lines 9–17). The patent specifically states at column 2, lines 37–43, that "[I]n the hydrogenation of oxides of carbon at pressures of 1,000 atmospheres and below, virtually no polyfunctional compounds are produced. At pressures above 1,000 atmospheres and especially at pressures of about 1,500 to 5,000 atmospheres, preferably 2,000 to 5,000 atmospheres, polyfunctional compounds are obtained."

The examples of the patent describe the use only of cobalt catalysts although the patent indicates that the catalyst may contain "cobalt, ruthenium, etc."

Gresham et al., U.S. Pat. No. 2,534,018, describe a process for preparing ethylene glycol by reacting carbon monoxide and hydrogen using a cobalt halide catalyst at a pressure of 3000 atmospheres and a temperature of 275° C. in a water/benzene solvent. Minor amounts of glycol formate were also reported.

Pruett and Walker, U.S. Pat. No. 3,833,634, patented Sept. 3, 1974, based on an application originally filed Dec. 21, 1971, describe a process for preparing glycols by reacting an oxide of carbon with hydrogen using a rhodium carbonyl complex catalyst. The examples of the patent compare the reaction of hydrogen and carbon monoxide in the presence of the desired rhodium containing catalyst and other metals. In Example 17 of the patent dicobalt octacarbonyl and acetic acid were charged to a reaction vessel and the reaction carried out. Traces of the mono- and diacetate of ethylene glycol were detected but no ethylene glycol was detected.

According to Roy L. Pruett, *Annals, New York Academy of Sciences*, Vol. 295, pages 239–248 (1977), at pages 245, metals other than rhodium were tested to determine the production of ethylene glycol from mixtures of carbon monoxide and hydrogen. These metals include cobalt, ruthenium, copper, manganese, iridium and platinum. Of these metals, only cobalt was found to have a slightly activity, citing British Pat. No. 665,698 which corresponds generally to U.S. Pat. No. 2,535,060. Pruett stated that such slight activity with cobalt was "qualitatively" in agreement with the results obtained by Ziesecke, 1952, Brennstoff-Chem, 33:385.

As pointed out above, ethylene glycol can be produced directly from a mixture of hydrogen and carbon monoxide using a rhodium carbonyl complex as a catalyst. There has been a substantial amount of work done on the formation of ethylene glycol from mixtures of hydrogen and carbon monoxide in the presence of rhodium carbonyl clusters. Such work is exemplified by the disclosures of U.S. Pat. Nos. 3,833,634; 3,878,214; and 3,878,290.

Further, the reaction of carbon monoxide and hydrogen in the presence of dioxane and a cobalt catalyst to give ethylene glycol was reported by H. M. Feder and J. S. Rathke, Ann. N.Y. Acad Sci., 333,45 (1980).

The preparation of glycol esters, such as ethylene glycol diesters, by the reaction of carbon monoxide and hydrogen in the presence of a ruthenium or osmium-containing catalyst and a liquid phase medium containing a carboxylic acid co-reactant is disclosed in U.S. Pat. No. 4,268,689, issued May 19, 1981. In comparative example XV of said patent the use of dicobalt octacarbonyl as the metal-containing catalyst formed methyl acetate (0.7 percent), ethyl acetate (2.7 percent), and glycol diacetate (0.1 percent). The process of U.S. Pat. No. 4,268,689 is carried out with a co-catalyst species selected from the group consisting of alkali metal salts, alkaline earth metal salts, quaternary ammonium salts, iminium salts and quaternary aliphatic phosphonium salts. The use of organosilicon compounds is not disclosed.

Several reports have been made wherein formaldehyde or $CH_2O$-containing compounds are reacted under a pressure of carbon monoxide and hydrogen in the presence of a cobalt catalyst to give glycolaldehyde, glycol, and their ethers. Exemplary of such reports are: J. A. Roth and M. Orchin, J. Organometal Chem., 172, C27 (1979), M. Muller-Cunradi, K. Pieroh, and L. Lorenz, German Pat. No. 890,945 (1953); K. Pieroh, German Pat. No. 875,802 (1953); U.S. Pat. No. 2,525,793 (1950) to W. F. Gresham and R. E. Brooks; U.S. Pat. No. 2,449,470 (1948) to W. F. Gresham and R. E. Brooks; U.S. Pat. No. 2,451,333 (1948) to W. F. Gresham and R. E. Brooks; K Hamada, K. Baba, and N. Hagihara, Osaka Univ. Inst. Sci. and Ind. Res. Mem., 14, 207 (1957); U.S. Pat. No. 4,079,085 (1978) to R. G. Wall; U.S. Pat. No. 3,920,753 to T. Yukawa and H. Wakamatsu; U.S. Pat. No. 4,071,568 to T. Onoda and S. Tomita; JA No. 51-128903 to T. Onada and S. Tomita; JA No. 52-73810 to T. Onoda and S. Tomita; JA No. 53-098917 (1978) to H. Shibata, S. Mori, Y. Ohkago, and T. Kameda; and H. M. Feder and J. S. Rathke, Ann. N.Y. Acad. Sci., 333,45 (1980). Unfortunately the aforementioned reactions require starting with formaldehyde or a $CH_2O$ containing compound and not with carbon monoxide and hydrogen.

The reaction of aldehydes having the formula RCHO (wherein R is $n-C_3H_7$, $n-C_6H_{13}$ or $c-C_6H_{11}$) with $CH_3(C_2H_5)_2SiH$ to give the product:

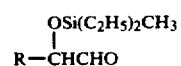

has been reported by S. Murai, T. Kato, N. Sonoda, Y. Seki, and K. Kawamoto, Abstr. A.C.S. Meeting, Honolulu, April 1979, No. 262; Agnew. Chem. International Ed., 18, 393 (1979). The reaction is carried out at room temperature under a pressure of 50 Kg/cm² in the presence of carbon monoxide, dicobalt octacarbonyl, and triphenylphosphine. Similarly, the aforementioned reactants have been reported by Y. Seki, S. Murai, and N. Sonoda, Agnew. Chem. International Edit., 17, 119 (1978) to produce:

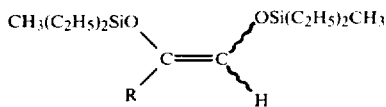

The high activity of cobalt as a catalyst in the present invention for the conversion of carbon monoxide and hydrogen to ethylene glycol and its derivatives as compared to the activity of cobalt reported earlier (see above) may be viewed in the light of a combination of the following: The reaction of $Co_2(CO)_8$ with $R_2SiH_2$ (R=ethyl, phenyl) to produce $(CO)_9Co_3COSiR_2Co(CO)_4$ has been reported [S. A. Fieldhouse, A. J. Clelland, B. H. Freeland, C. D. M. Mann, and R. J. O'Brien, J. Chem. Soc. (A), 2536 (1971)]; K. Tominaga, N. Yamagami, and H. Wakamatsu, Tet. Lett., 2217 (1970) and G. Fachinetti, U.S. application Ser. No. 12,612, commonly assigned, have reported that $(CO)_9Co_3C$—Y reacts with carbon monoxide and hydrogen to give products having one carbon atom and one oxygen atom more than C—Y e.g., $(CO)_9Co_3C$—$OCH_3 \rightarrow HOCH_2C$-$H_2OCH_3$; it has been reported [J. A. Gladysz, J. C. Selover, and C. E. Strouse, J. Am. Chem. Soc., 100, 6766 (1978)] that an alpha-trimethylsilyloxy substituent can accelerate carbonylation of an alkyl group.

In copending application U.S. Ser. No. 278,899, filed concurrently herewith, a process is disclosed for the manufacture of ethylene glycol, methanol, and derivatives thereof from the reaction of hydrogen and carbon monoxide by a homogeneous catalytic process using as the catalyst a ruthenium containing compound and an organosilicon compound having a hydrogen bonded to silicon (—Si—H).

In copending application U.S. Ser. No. 278,898, filed concurrently herewith is disclosed a process for the manufacture of alcohols and derivatives thereof from the carbon residue of an organosilicon compound wherein such alcohol has one carbon and one oxygen more than the corresponding carbon residue from which it was derived.

Owing to the reduced availability of petroleum sources the cost of producing chemicals from petroleum has been steadily increasing. Many have raised the dire prediction of significant oil shortages in the future. Obviously a different low cost source is needed which can be converted into the valuable chemicals now derived from petroleum sources. Synthesis gas is one such source which can be effectively utilized in certain circumstances to make chemicals.

The most desirable aspect of synthesis gas is that it can be produced from non-petroleum sources. Synthesis gas is derived by the combustion of any carbonaceous material including coal, or any organic material, such as hydrocarbons, carbohydrates and the like. Synthesis gas has for a long time been considered a desirable starting material for the manufacture of a variety of chemicals and, as discussed hereinabove, homogeneous cobalt-containing catalysts will produce ethylene glycol and methanol directly from synthesis gas.

However, while previously no processes using homogeneous cobalt catalysts will produce ethylene glycol and other polyhydric alcohols, generally very high pressure is required and it would be desirable to produce ethylene glycol and methanol or derivatives thereof at high process efficiency and low or moderate pressures.

SUMMARY OF THE INVENTION

In accordance with the present invention there is provided a process for preparing ethylene glycol, methanol, and derivatives thereof which comprises reacting a mixture comprising oxides of carbon and hydrogen in the presence of a catalytically effective amount of a cobalt catalyst and an organosilicon compound having at least one silicon atom bonded to hydrogen (Si—H).

It has been found that when ethylene glycol and methanol were prepared in accordance with the present invention that the production of ethylene glycol, methanol and derivatives thereof can be achieved under pressure and temperature conditions not possible when only a cobalt catalyst is employed.

DESCRIPTION OF THE INVENTION

This process constitutes a relatively low pressure process for converting synthesis gas to ethylene glycol, methanol, and derivatives thereof. The process of this invention is carried out with a cobalt catalyst and organosilicon compound in solution, even though the cobalt catalyst may exist during the reaction in more than one liquid phase. In this sense, the reaction is termed a homogeneous liquid phase reaction. There may be more than one such phase existing in the reaction zone but the catalyst is always dissolved in at least one of such phases and is always in a dissolved liquid state.

The process of this invention involves the reaction of synthesis gas in the presence of soluble cobalt catalyst and the organosilicon compound at temperatures and pressures for a period of time sufficient to produce ethylene glycol, methanol, and derivatives thereof under such conditions as set forth herein. The reaction conditions comprise (i) a period of time at a temperature and pressure which cause the hydrogen and carbon monoxide to react to produce the desired product, (ii) preferably a temperature between about 50° C. and 400° C. and more preferably between about 100° C. and 350° C., and (iii) preferably a pressure between about 100 psia (7.0 Kg/cm²) and 15,000 psia (1,054.6 Kg/cm²) and more preferably between about 500 psia (35.15 Kg/cm²) and 12,500 psia (878.84 Kg/cm²). The catalyst of this invention is a cobalt catalyst and organosilicon compound having at least one Si—H bond which under the prescribed reaction conditions catalyzes the aforementioned reaction between carbon monoxide and hydrogen.

The cobalt catalyst of this invention may comprise any cobalt containing compound which provides a homogeneous cobalt catalyst under the process conditions. Suitable cobalt containing compounds include cobalt carbonyl compounds such as dicobalt octacarbonyl, cobalt salts of organic and inorganic acids, cobalt oxides and the like.

The selection of the organosilicon compound, i.e. silane, is such that the compound contains at least one bond between a silicon atom and a hydrogen atom. Typical of suitable organosilicon compounds are silanes, mono-, di- and trialkyl silanes, e.g. trihexylsilane, wherein said alkyl substituents may be substituted. In general the organosilicon compound is selected such that at least one —Si—H bond is present and may include silicon derived polymers having at least one silicon bonded to hydrogen. Representative compounds which are suitable for use in the instant process are set forth in E. Wiberg and E. Amberger, "Hydrides of Elements of Main Groups I-IV," Elsevier, 1971, pages 462-638; and V. Bazant and V. Chvalovsky, "Chemistry of Organosilicon Compounds," vol. 1 of V. Bazant, V. Chvalovsky, and J. Rathousky, "Organosilicon Compounds," Academic Press, 1965, p. 102-151, said disclosures to said suitable organosilicon compounds being incorporated by reference herein. The following organosilicon compounds are illustrative of those which may be employed herein:

$H_3SiCH_2SiH_3$ $H_3SiCH_2CH_2SiH_3$ $CH_3SiH_2CH_2SiH_3$ $CH_3SiH_2CH_2SiH_2$
$|$
$CH_3SiH_2CH_2$

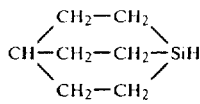

$C_6H_{11}SiH_3$ $CH_3CH=CHCH_2SiH_3$ $CH_2=CHCHSiH_3$
$|$
$CH_3$ $CH_2=CHCH_2SiH_3$ $C_6H_5CH_2CH_2SiH_3$ $C_6H_5CH(CH_3)SiH_3$ $(C_3H_7)_2SiH_2$ $(CH_3)(iso\text{-}C_4H_9)SiH_2$ $(C_2H_5)(iso\text{-}C_4H_9)SiH_2$ $(CH_2=CH)(C_2H_5)SiH_2$ $(CH_2=CH)(C_4H_9)SiH_2$ $(CH_2=CHCH_2)_2SiH_2$ $(CH_3)(CH_2=CHCH)SiH_2$
$|$
$CH_3$ $(C_2H_5)_2SiH_2$ $\begin{array}{c} CH_2-CH_2 \\ | \quad\quad\quad \searrow \\ \quad\quad\quad\quad SiH_2 \\ | \quad\quad\quad \nearrow \\ CH_2-CH_2 \end{array}$ $(C_2H_5)_3SiH$ $(CH_2=CH)(C_2H_5)_2SiH$ $(C_6H_{13})_3SiH$ $(CH_3)_2(CH_2=CH)SiH$ $(C_2H_5)_2(CH_2=CH)SiH$ $(C_6H_5)_2(CH_2=CH)SiH$ $(CH_3)(C_6H_5)(CH_2=CH)SiH$ $(m\text{-}CH_3C_6H_4)_3SiH$ $(p\text{-}CH_3OC_6H_4)_3SiH$ $[m\text{-}(CH_3)_2NC_6H_4]_3SiH$ $(p\text{-}CH_3OC_6H_4)_3SiH$ $[p\text{-}(CH_3)_2NC_6H_4]_3SiH$ $(p\text{-}ClC_6H_4)_3SiH$ $\begin{array}{c} \quad CH_2-CH_2 \\ \diagup \quad\quad\quad \diagdown \\ CH-CH_2-CH_2-SiH \\ \diagdown \quad\quad\quad \diagup \\ \quad CH_2-CH_2 \end{array}$ $H_3SiCH_2CH_2SiH_3$ $(F_3CCH_2CH_2)(CH_3)_2SiH$ $(F_3CCH_2CH_2CH_2)(CH_3)_2SiH$ $(F_3CCH_2CH_2)_2(CH_3)SiH$ $(C_3H_7)_3SiH$ $(C_6H_5)_3SiH$ $(C_2H_5)_2SiH_2$ $(CH_3)(C_3H_7)SiH_2$ $(CH_3)_2(iso\text{-}C_3H_7)SiH$ $C_4H_9SiH_3$ $iso\text{-}C_4H_9SiH_3$ $sec\text{-}C_4H_9SiH_3$ As characterized above, this process is operated as a homogeneous liquid phase mixture. The process is typically carried out in a solvent for the catalyst. The solvent may be solid at room temperature but should at least, in part, be a liquid under the conditions of reaction.

Apart from the conditions of the reaction in terms of time, temperature and pressure, the selection of solvent may constitute an important consideration in the most advantageous practice of this invention. The selection of solvents is not clearly understood but is not believed to be narrowly limited. The solvent is selected such that the solvent is capable of maintaining the cobalt catalyst in the homogeneous liquid phase mixture throughout the reaction.

Illustrative of suitable solvents are, e.g., ketones, esters including lactones, amides including lactams, sulfones, sulfoxides, aromatic hydrocarbons, and the like. Illustrative of specific solvents encompassed by the above classes of solvents are, for example, aromatic hydrocarbons, e.g., benzene, toluene, xylene, naphthalene, alkylnaphthalene, etc; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; anhydrides such as phthalic anhydride, acetic anhydride, etc.; lactams such as N-alkyl caprolactam, such as N-methylcaprolactam; N- alkyl pyrrolidinones, such as N-methyl pyrrolidinone, cyclic ureas such as N,N'-dimethylimidazolidone; lactones such as gamma-butyrolactone; amides such as dimethylformamide, dimethylacetamide, hexamethylphosphoramide; sulfones such as sulfolane, dimethylsulfone, the substituted sulfolanes described in U.S. Pat. No. 4,224,237; sulfoxides such as dimethylsulfoxide, diphenyl sulfoxide; as well as many others.

Illustrative of other suitable solvents are the ethers, and the like. Illustrative of specific solvents encompassed by the above class of solvents are, for example, ethers such as tetrahydrofuran, tetrahydropyran, diethyl ether, 1,2-dimethoxybenzene, 1,2-diethoxybenzene, the dialkyl ethers of alkylene and polyalkylene glycols, such as ethylene glycol, of 1,2-propylene glycol, of 1,2-butylene glycol, of diethylene glycol, of di-1,2-propylene glycol, of triethylene glycol, of pentaethylene glycol (such as triglyme, tetraglyme and pentaglyme), of di-1,2-butylene glycol, of oxyethylene-oxypropylene glycols, etc., preferably those in which the alkylene group contains 2 and/or 3 carbon atoms in the divalent moiety, such as ethylene and 1,2-propylene; the crown ethers such as described in U.S. Pat. No. 4,162,261, which description of crown ethers, as solvents in that case, are incorporated herein by reference; as well as many others.

In addition, the solvent employed in the practice of this invention may comprise a mixture of two or more of the aforementioned solvents. Which mixtures will achieve what result has not been determined.

The process may be carried out in the presence of a promoter although selection of the promoter is not clearly understood. A promoter, in the context of this invention, is a material provided to the reaction which provides a promotional effect in that it enhances the production (viz., rate, yield, or efficiency) of any of the products, or it improves the selectivity of the reaction toward ethylene glycol rather than methanol or it helps to reduce the loss of cobalt during the reaction.

Though the process of this invention is capable of providing a combination of ethylene glycol and methanol and derivatives thereof, in many instances one or more of them is formed as a minor component only. Because ethylene glycol is the most valued of the products, its production obviously makes this process attractive. Formation of methanol also enhances the commercial attractiveness of this process.

The relative amounts of carbon monoxide and hydrogen which are initially present in the reaction mixture can be varied over a wide range. In general, the molar ratio of $CO:H_2$ is in the range of from about 40:1 to about 1:40, suitably from about 20:1 to about 1:20, and preferably from about 10:1 to about 1:10. It is to be understood, however, that molar ratios outside the broadest of these ranges may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention.

The quantity of cobalt catalyst and the quantity of organosilicon catalyst employed are not narrowly critical and can vary over a wide range. In general, the process is desirably conducted in the presence of a catalytically effective quantity of each catalyst which gives a suitable and reasonable reaction rate.

The reaction may proceed when employing as little as about $1 \times 10^{-6}$ weight percent, and even lesser amounts, of each catalyst, based on the total weight of reaction mixture (i.e., the liquid phase mixture). The upper concentration limit can be quite high, e.g., about 30 weight percent, and higher of the cobalt catalyst and up to about 100 percent by weight of the organosilicon catalyst, e.g., when the organosilicon catalyst is also employed as the solvent; the realistic upper limit in practicing the invention would appear to be dictated and controlled more by economics of the process, since the rate of conversion of synthesis gas may be dependent upon the concentration of catalyst employed. Since higher concentrations may achieve higher rates, large concentrations may prove to be a most desirable embodiment of this invention. Depending on various factors such as the partial pressures of carbon monoxide and hydrogen, the total operative pressure of the system, the operative temperature, the choice of solvent, and other considerations, a catalyst concentration of from about $1 \times 10^{-3}$ to about 20 weight percent each of the cobalt catalyst and up to about 100 percent by weight of the organosilicon catalyst, e.g., when the organosilicon catalyst is also employed as the solvent, based on the total weight of reaction mixture, is generally desirable in the practice of the invention. The actual concentration which will provide for the formation of the products of the instant process will depend on several factors and for a given organosilicon compound a concentration greater than $1 \times 10^{-3}$ may be required to provide for the formation of methanol, ethylene glycol and derivatives thereof.

The temperature which may be employed in practicing the process may vary over a wide range of elevated temperatures. In general, the process can be conducted at a temperature between 50° C. and about 400° C. and higher. Temperatures outside this stated range, though not excluded from the scope of the invention, do not fall within certain desirable embodiments of the invention. The examples below depict batch reactions; however, a continuous gas recycle process can be operated in a similar manner. That is, the batch reactor simulates the continuous reactor except for the gas sparging and continuous gas recycle.

Although this invention has been described with respect to a number of details, it is not intended that this invention should be limited thereby. Moreover, the examples which follow are intended solely to illustrate a variety, including the most favorable, embodiments of this invention and are not intended in any way to limit the scope and intent of this invention.

EXPERIMENTAL PROCEDURE

The following examples, except for examples 21 and 22, were carried out according to the following procedure:

A 150 ml. capacity stainless steel reactor capable of withstanding pressures up to 7,000 atmospheres was charged with a specified organosilicon compound and a specified amount of a metal compound as indicated in the tables. The reactor was sealed and charged with a gaseous mixture containing equal molar amounts of carbon monoxide and hydrogen to a desired pressure. Heat was applied to the reactor and its contents; when the temperature of the mixture inside the reactor reached 190° C., as measured by a suitably placed thermocouple, an additional adjustment of carbon monoxide and hydrogen ($H_2:CO = 1:1$ mole ratio) was made to bring the pressure back to that which is specified in the examples. The temperatures and pressures were maintained as indicated in the examples.

After the reaction was terminated, the reactor and its contents were cooled to room temperature, the excess gas vented and the reaction product mixture was removed. The reactor was then washed with acetone. The reaction mixture and wash were analyzed by use of vapor phase chromatography (VPC) and nuclear magnetic resonance (NMR) spectroscopy.

The reaction mixture (1.0 gram of the reaction mixture) was treated with benzoic anhydride (0.73 gram) by placing the reaction mixture and the benzoic anhydride in a glass tube which was then sealed with a rubber septum and a cap. The mixture was shaken and then heated to about 250° C. in an oil bath for about 1 hour. The mixture was then cooled to ambient conditions and dissolved in 3 milliliters of $CDCl_3$ prior to analysis by VPC and NMR.

The effect of the concentration of benzoic anhydride was studied and the aforementioned procedure determined to be adequate. The results reported in the following examples are based on these analyses, i.e., the results are the amounts of methyl benzoate and glycol dibenzoate (identification based on VPC retention time and NMR and mass spectra) detected but are expressed and reported as the methanol and ethylene glycol equivalents. The treatment of the reaction mixture is based on a report [A. Ladenburg, Ber., 5, 319 (1872)] of the reaction $(C_2H_5)_3SiOC_2H_5 + (CH_3CO)_2O$ to give $(C_2H_5)_3Si\text{-}OCOCH_3 + C_2H_5OCOCH_3$.

The efficiency of the treatment of the reaction mixture with benzoic anhydride was studied by heating a representative silane (0.40 gram, 3.2 millimoles, of trimethylethoxysilane) with 0.73 gram of benzoic anhydride at 250° C. for 1 hour in a totally-immersed sealed tube. The NMR spectrum of the reaction mixture indicated a 77 percent conversion to ethyl benzoate. Similarly, $(C_6H_{13})_3SiOCH_2CH_2OSi(C_6H_{13})_3$ (0.11 g, 0.177 millimole) was heated with 0.73 gram of benzoic anhydride and 1.000 gram (3.5 millimoles) of trihexylsilane with a 57 percent conversion to glycol dibenzoate observed. In addition, according to the above procedure, 0.112 gram of $(C_6H_{13})_3SiOCH_2CH_2OSi(C_6H_{13})_3$ and 1.003 grams of trihexylsilane were treated with benzoic anhydride with a 62 percent conversion to glycol dibenzoate observed.

In examples 21 and 22 the following procedure was employed:

A 150 ml stainless steel reactor capable of withstanding pressures up to 10,000 psig and containing a removal glass liner was charged with a cobalt compound (as designated below in the examples). The reactor was purged with carbon monoxide and pressurized with an initial charge of 500 psig (36.19 $Kg/cm^2$) of carbon monoxide. Carbon monoxide and hydrogen (1:1 mole ratio) were then added to the reactor to attain the desired pressure. The reactor was rocked and the contents heated to the reaction temperature and maintained at the reaction temperature for two hours while rocking the reactor. The pressure was maintained at the specified reaction pressure during the indicated period of the reaction by adding carbon monoxide and hydrogen. With these added repressurizations the pressure inside the reactor was maintained at the reaction pressure over the reaction period. The reactor was then cooled and vented. The contents of the reactor were removed and analyzed as above-described.

The preparation of the bis(trihexylsilyl) ether of ethylene glycol was carried out by reacting ethylene glycol (2.4 grams, 0.039 mole) (stirred with NaOH, then distilled at 92° C./10 mm), trihexylchlorosilane (25 grams, 0.078 mole) and pyridine (7.8 milliliters, 0.097 mole) refluxed over NaOH, then distilled at 113° C. and stored over $CaH_2$) in 47 milliliters of toluene (dried over conventional molecular sieves) according to the procedure described by R. O. Sauer, J: Am. Chem. Soc., 66, 1707 (1944) for the preparation of $(CH_3)_3SiOCH_3$ which is incorporated herein by reference. Five grams of the crude product (having a total weight of about 25 grams) was purified by chromatography using 200 grams of Woelm (TM) silica gel. A final product of at least 1.5 grams was obtained. [NMR ($CDCl_3$): 3.63 (s,2.OH), 5.6-7.2(m,39H) ppm upfield from $CHCl_3$; Chemical ionization (isobutane) mass spectrum: calculated for $C_{38}H_{82}O_2Si_2$ 626.5853, for $C_{38}H_{82}O_2Si_2—C_6H_{13}$ 541.4835; found 626.5198±66 ppm (parent), 541.4828±1.3 ppm (base)].

EXAMPLES 1–10

Comparative examples 1–8 and 10 were carried out by charging 80 milliliters of trihexylsilane and the metal catalyst shown in Table I. The reaction was carried out under a carbon monoxide and hydrogen atmosphere (1:1 mole ratio of $H_2:CO$) under a pressure of 8000 psig for a period of 4 hours. Samples were tested at 1 hour, 2 hours and 4 hours after the reaction had begun. Example 9 is carried out according to this invention. The results of examples 1–10 are set forth in Table I.

TABLE I

| Example | Silane | Metal catalyst | mmoles of Metal catalyst | Product(1 hr.)[1] MeOH[2] | Product(1 hr.)[1] GLYCOL[2] | Product(2 hr.)[1] MeOH[2] | Product(2 hr.)[1] GLYCOL[2] | Product(4 hr.)[1] MeOH[2] | Product(4 hr.)[1] GLYCOL[2] |
|---|---|---|---|---|---|---|---|---|---|
| 1 | $(C_6H_{13})_3SiH$ | — | | PT[6] | PT | VS | PT | 0.23 | — |
| 2 | $(C_6H_{13})_3SiH$ | $Rh(CO)_2acac$ | 3.0 | 0.26 | 0.79 | 0.29 | 0.63 | 0.45 (0.5) | 0.50 (0.1) |
| 3[2] | $(C_6H_{13})_3SiH$ | $ClRh(CO)(Ph_3P)_2$ | 3 | ≦VS[6] | — | 0.18 | — | 0.33 | — |
| 4[4] | $(C_6H_{13})_3SiH$ | $Mn_2(CO)_{10}$ | 1.5 | 0.28 | — | 0.18 | — | 0.38 | T[6] |
| 5[3] | $(C_6H_{13})_3SiH$ | $Cu_2O$ | 1.5 | VS | — | 0.29 | — | 0.28 | T |
| 6[4] | $(C_6H_{13})_3SiH$ | $H_2PtCl_6.6H_2O$ | 3 | S[6] | T | 0.18 | — | 0.14 | T |
| 7 | $(C_6H_{13})_3SiH$ | $H_2OsCl_6.2H_2O$ | 3 | ND[5] | ND[5] | 0.85 | — | 0.31 | — |
| 8[2] | $(C_6H_{13})_3SiH$ | $[Ph_3P]_2PdCl_2$ | 3 | — | — | S | — | 0.28 | — |
| 9 | $(C_6H_{13})_3SiH$ | $Co(CO)_8$ | 1.5 | 0.38 | 0.62 | 0.49 | 0.76 | 0.56 (0.1) | 0.50 |

TABLE I-continued

| Example | Silane | Metal catalyst | mmoles of Metal catalyst | Product(1 hr.)[1] MeOH[2] | GLYCOL[2] | Product(2 hr.)[1] MeOH[2] | GLYCOL[2] | Product(4 hr.)[1] MeOH[2] | GLYCOL[2] |
|---|---|---|---|---|---|---|---|---|---|
| 10 | $(C_6H_{13})_3SiH$ | $Ru_3(CO)_{12}$ | 1.0 | 1.4 | 0.41 | 2.1 | 0.59 | 3.9 | 0.64 |

[1]Given in grams and uncorrected for incomplete derivatization. The numbers in parentheses are additional amounts, not subject to correction, found in a small denser phase which accompanied the reaction mixture or found in the acetone wash of the reactor.
[2]Glycol = Ethylene glycol; MeOH = methanol; Ph = phenyl
[3]Copper plates the reactor
[4]Gas evolved upon mixing at room temperature
[5]Not determined
[6]PT = perhaps trace; T = trace; VS = very small; and S = small

EXAMPLES 11-20

Examples 11-20 were carried out according to the above described experimental procedure using 80 milliliters of trihexylsilane wherein the trihexylsilane was heated at 270° C. for 4 hours in the presence of cobalt catalyst under an atmosphere of carbon monoxide and hydrogen (1:1 mole ratio). The pressure employed in each example is set forth in Table II with the quantity of methanol and ethylene glycol as determined after 1 hour, 2 hours and 4 hours after the reaction had commenced. The cobalt compound employed in examples 12-20 was dicobalt octacarbonyl. Example 11 is a comparative example wherein no cobalt compound was employed.

EXAMPLES 23-32

Examples 23-32 were carried out according to the above-described experimental procedure except that the solvent comprised 75 milliliters of sulfolane and was heated at 250° C. for 4 hours under a pressure of carbon monoxide and hydrogen (8000 psig) in the presence of 1.5 millimoles of dicobalt octacarbonyl. In examples 24-30 a organosilicon compound was added as indicated in Table IV.

TABLE III

| Example | Silane | mmoles of $Co_2(CO)_8$ | PRESSURE(psig) | Product(1 hr)[1] MeOH[2] | GLYCOL[2] | Product(2 hrs)[1] MeOH | GLYCOL | Product(4 hrs)[1] MeOH | GLYCOL |
|---|---|---|---|---|---|---|---|---|---|
| 21 | $(C_6H_{13})_3SiH$ | — | 4900 | ND[3] | ND | ND | ND | 0.31 | 0 |
| 22 | $(C_6H_{13})_3SiH$ | 1.0 | 5000 | ND | ND | ND | ND | 0.85 | 0.79 |

[1]Given in grams and uncorrected for incomplete derivatization.
[2]MeOH = methanol; and GLYCOL = ethylene glycol
[3]ND = Not Determined

TABLE IV

| Example | Organosilicon Compound | mmoles[2] | Methanol | Glycol |
|---|---|---|---|---|
| 23 | — | — | —[4] | 0 |
| 24 | $(C_6H_{13})_3SiH$ | 5 | PT[3] | 0 |
| 25 | $(C_6H_{13})_3SiH$ | 30 | PT | 0 |
| 26 | $Et_2SiH_2$ | 5 | PT | 0 |
| 27 | $Ph_3SiH$ | 5 | 0 | 0 |
| 28 | $Ph_2SiH_2$ | 5 | PT | 0 |
| 29 | $PhSiH_3$ | 5 | PT | 0 |
| 30 | $(EtO)_3SiH$ | 5 | 0 | 0 |
| 31 | $Ph_3GeH$ | 5 | 0 | 0 |
| 32 | $Bu_3SnH$ | 5 | 0 | 0 |

[1]Ph = phenyl; Et = $C_2H_5$; Bu = n-butyl; Glycol = ethylene glycol
[2]mmoles of organosilicon compound
[3]PT = perhaps trace
[4]Possibly very small amount

TABLE II

| Example | Silane | mmoles of $Co_2(CO)_8$ | PRESSURE(psig) | Product(1 hr)[1] MeOH[2] | GLYCOL[2] | Product(2 hrs)[1] MeOH | GLYCOL | Product(4 hrs) MeOH | GLYCOL |
|---|---|---|---|---|---|---|---|---|---|
| 11 | $(C_6H_{13})_3SiH$ | — | 6300 | T[3] | 0 | T[3] | 0 | VS[3] (0.3) | 0 |
| 12 | $(C_6H_{13})_3SiH$ | 1.5 | 6000 | 0.36 | 0.48 | 0.33 | 0.77 | 0.28 (0.2) | 0.73 (0.3) |
| 13 | $(C_6H_{13})_3SiH$ | 6 | 6000 | 0.38 | 0.55 | 0.33 | 0.61 | 0.26 (0.1) | 0.35 |
| 14 | $(C_6H_{13})_3SiH$ | 1.5 | 8000 | 0.38 | 0.62 | 0.49 | 0.76 | 0.52 (0.3) | 0.50 (0.2) |
| 15 | $(C_6H_{13})_3SiH$ | 1.5 | 6000 | 0.36 | 0.48 | 0.33 | 0.77 | 0.28 | 0.73 |
| 16 | $(C_6H_{13})_3SiH$ | 1.5 | 4000 | 0.21 | 0.19 | 0.23 | 0.23 | 0.21 | 0.26 |
| 17 | $(C_6H_{13})_3SiH$ | 1.5 | ~2400 | 0 | 0 | T | 0 | 0.11 (0.2) | 0.083 (0.3) |
| 18 | $(C_6H_{13})_3SiH$ | 6 | 6000 | 0.38 | 0.55 | 0.33 | 0.61 | 0.26 (0.1) | 0.35 (0.3) |
| 19 | $(C_6H_{13})_3SiH$ | 6 | 5000 | 0.55 | 0.59 | 0.50 | 0.91 | 0.44 (0.4) | 0.76 |
| 20 | $(C_6H_{13})_3SiH$ | 6 | 4000 | 0.69 | 0.51 | 0.45 | 0.46 | 0.31 | 0.33 |

[1]Given in grams and uncorrected for incomplete derivatization. The numbers in parentheses are additional amounts, not subject to correction, found in a small denser phase which accompanied the reaction mixture or found in the acetone wash of the reactor.
[2]MeOH = methanol; and GLYCOL = ethylene glycol
[3]PT = perhaps trace; T = trace; VS = very small; and S = small

EXAMPLES 21 and 22

Example 21 and Example 22 were carried out according to the invention using 50 milliliters of trihexylsilane under a pressure of carbon monoxide and hydrogen (1:1 mole ratio) at 270° C., for 4 hours at which time the amount of methanol and ethylene glycol formed was determined. The results of examples 21 and 22 are set forth in Table III.

EXAMPLES 33-35

Examples 33-35 were carried out by employing 80 milliliters of the solvent indicated in Table V at 270° C. for 4 hours in the presence of 1.5 millimoles of dicobalt octacarbonyl. The amount of methanol and ethylene glycol detected at 4 hours is set forth in Table V.

TABLE V

| Example | Solvent | Methanol[1] | GLYCOL[2] | Pressure (psig) |
|---|---|---|---|---|
| 33 | Sulfolane | 0.2 | 0 | 6200 |
| 34 | Dibutyl Ether | 0.5 | 0 | 6200 |
| 35 | $(C_2H_5)_4Si$ | <0.1 | 0 | 6000 |

[1] Given in grams and uncorrected for incomplete derivatization.
[2] GLYCOL = ethylene glycol.

EXAMPLE 36

Example 36 was carried out in the same manner as employed in examples 11-20 except that 75 grams of triphenylsilane was substituted for trihexylsilane. The pressure was 6000 psig and 1.5 millimoles of dicobalt octacarbonyl was employed. The amount of methanol and ethylene glycol (in grams) was determined at 1 hour, 2 hours, and 4 hours, by the method previously discussed, and was as follows:

|  | Methanol | Glycol |
|---|---|---|
| 1 hour | 0.19 | trace |
| 2 hours | 0.20 | 0.25 |
| 4 hours | 0.16 | 0.12 |

What is claimed is:

1. The process for making the products ethylene glycol, methanol, and derivatives thereof directly from the reaction of hydrogen and carbon monoxide which comprises reacting a mixture comprising oxides of carbon and hydrogen in the homogeneous liquid phase containing an effective amount of a cobalt-containing compound and an organosilicon compound having at least one hydrogen bonded to silicon wherein said process is carried out for a period of time at a temperature and pressure which cause the carbon monoxide and hydrogen to react to produce, ethylene glycol, methanol, and derivatives thereof.

2. The process of claim 1 wherein the temperature is between about 50° C. and 400° C.

3. The process of claim 2 wherein the temperature is between about 100° C. and about 350° C.

4. The process of claim 1 wherein the pressure is between about 100 psia (7.0 Kg/cm) and 15,000 psia (1,054.6 Kg/cm).

5. The process of claim 4 wherein the pressure is between about 500 psia (35.15 Kg/cm$^2$) and 12,500 psia (878.84 Kg/cm$^2$).

6. The process of claim 1 wherein the pressure is the total pressure of hydrogen and carbon monoxide supplied to said process.

7. The process of claim 1 wherein a solvent is employed.

8. The process of claim 1 wherein unreacted carbon monoxide and hydrogen are recycled to the liquid phase.

9. The process of claim 1 wherein the cobalt-compound is a cobalt carbonyl.

10. The process of claim 1 wherein the organosilicon compound is a trialkylsilane.

11. The process of claim 1 wherein the concentration of said cobalt-containing compound and of said organosilicon compound is between about $1 \times 10^{-6}$ percent by weight and about 30 percent by weight.

12. The process of claim 7 wherein the solvent is the organosilicon compound.

13. The process of claim 1 wherein the organosilicon compound is a mono-, di-, or tri-alkyl silane.

14. The process of claim 13 wherein the organosilicon compound is a trialkylsilane.

15. The process of claim 14 wherein the organosilicon compound is trihexylsilane.

* * * * *